United States Patent
Zhang et al.

(10) Patent No.: US 10,781,186 B2
(45) Date of Patent: Sep. 22, 2020

(54) METHOD OF SYNTHESIZING 1,2,4-TRIAZOLE-3-THIONE COMPOUNDS AND INTERMEDIATES THEREOF

(71) Applicant: ORIENTAL (LUZHOU) AGROCHEMICALS CO., LTD., Luzhou, Sichuan (CN)

(72) Inventors: Zhiming Zhang, Sichuan (CN); Xiaodong Du, Sichuan (CN); Qiuju Sheng, Zhejiang (CN); Jieping Shi, Zhejiang (CN); Junliang Wang, Zhejiang (CN); Bangchi Chen, Zhejiang (CN)

(73) Assignee: ORIENTAL (LUZHOU) AGROCHEMICALS CO., LTD., Luzhou, Sichuan (CN)

(*) Notice: Subject to any disclaimer, the term of this patent is extended or adjusted under 35 U.S.C. 154(b) by 0 days.

(21) Appl. No.: 16/212,705

(22) Filed: Dec. 7, 2018

(65) Prior Publication Data
US 2019/0127338 A1     May 2, 2019

Related U.S. Application Data

(63) Continuation of application No. PCT/CN2016/090129, filed on Jul. 15, 2016.

(51) Int. Cl.
*C07D 249/12* (2006.01)

(52) U.S. Cl.
CPC .................. *C07D 249/12* (2013.01)

(58) Field of Classification Search
CPC .................................................. C07D 249/12
See application file for complete search history.

(56) References Cited

U.S. PATENT DOCUMENTS 4,659,644 A     4/1987  Hoshina et al.

FOREIGN PATENT DOCUMENTS

| CN | 1274346 A | 11/2000 | |
|---|---|---|---|
| CN | 101547916 A | 9/2009 | |
| CN | 105636441 A | 6/2016 | |
| WO | WO/2015/152367 A2 * | 10/2015 | ........... C07D 401/06 |

OTHER PUBLICATIONS

Guan, Yunfei et al. "A Review of Synthetic Method of Prothioconazole" Agrochemicals, vol. 53, No. 9, Sep. 30, 2014 (Sep. 30, 2014) pp. 696 to 698.
Vaillancourt, V.A. et al. "Synthesis and Biological Activity of Aminoguanidine and Diaminoguanidine Analogues of the Antidiabetic/Antiobesity Agent 3-Guanidinopropionic Acid" Journal of Medicinal Chemistry, vol. 44, No. 8, Mar. 10, 2001.

* cited by examiner

*Primary Examiner* — Joseph R Kosack
(74) *Attorney, Agent, or Firm* — Wayne & Ken, LLC; Tony Hom

(57) ABSTRACT

Disclosed is a method of synthesizing 1,2,4-triazole-3-thione compounds and intermediates thereof. The method includes reacting a hydrazine with glyoxylic acid to form a hydrazono acetic acid intermediate followed by reacting the latter with thiocyanate to obtain the 1,2,4-triazole-3-thione compound. The raw materials involved in the present method are readily available, and the reaction is very specific in terms of regioselectivity, resulting in minimum by-product and high product yield. There are neither specific requirements for special equipment nor special operations such as high vacuum, high temperature, anhydrous and oxygen-free manipulations. The process is simple and generates minimum wastes, suitable for industrial production.

13 Claims, No Drawings

METHOD OF SYNTHESIZING 1,2,4-TRIAZOLE-3-THIONE COMPOUNDS AND INTERMEDIATES THEREOF

CROSS-REFERENCE TO RELATED APPLICATIONS

This application is a continuation of International Patent Application No. PCT/CN2016/090129, filed on Jul. 15, 2016, which is incorporated herein by reference in its entirety.

TECHNICAL FIELD

The present disclosure relates to organic synthesis, and more specifically to a method of synthesizing 1,2,4-triazole-3-thione compounds and intermediates thereof.

BACKGROUND 1,2,4-Triazole-3-thione compounds 1 is a class of materials with significant biological activities.

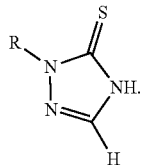

For example, it has been discovered that 1,2,4-triazole-3-thiones 1 have antibacterial activities (WO 2010142779, WO 2010146113, WO 2010146111, WO 2010146112, WO 2010040717, WO 2014167008, WO 2010040718, WO 9706152, W9638423, WO 9616048, WO 9641798, WO 9741107, WO 2010149758, EP 2746260, WO 2010146029, WO 2009077471, IN 193553, WO 2009077500 and WO 2014108288), antiviral activities (WO 2010149758, WO 2010122169, WO 2010142779, WO 2010149414 and WO 2010122167), antitumor activities (WO 2010149758, WO 2010122169, WO 2010142779, WO 2010149414 and WO 2010122167), and other biological activities (WO 2013047308, WO 2013084770 and WO 2011125317), and etc.

Strategy of synthesizing 1,2,4-triazole-3-thione compounds 1 can be classified into two categories according to the way that the triazole ring is constructed. The first strategy of producing target triazole-thione product is through cyclization of thiosemicarbazide with formic acid or formic acid derivatives. For example, reaction of N-amino-N-methylthiourea (compound 2, R is methyl) with formic acid gives 2-methyl-1,2,4-triazole-3-thione product (Justus Liebigs Annalen der Chemie, 643, 128-35; 1961). This method displays high efficiency in terms of the ring formation reaction, however, the preparation of compound 2 is very challenging, regioselectivity is usually a problem.

The second strategy of producing 1,2,4-triazole-3-thione compounds 1 is through modification of the already constructed triazole ring. For example, deprotonation of N-phenyltriazole (compound 3, R is phenyl) with lithium tert-butoxide followed by reaction with sulfur gives the target product (Journal of Organic Chemistry, 74(21), 8309-8313; 2009). This reaction requires the use of a strong organic base during the deprotonation processes, as well as manipulation under anhydrous and oxygen-free conditions, and regioselectivity of the deprotonation process is also a problem.

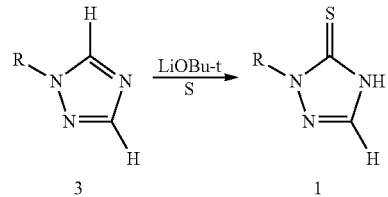

Heteroatom Chemistry, 14(1), 50-55; 2003 reported a method for the preparation of 1,2,4-triazole-3-thione compounds 1 using compound 4 through flash vacuum pyrolysis (FVP). This method requires not only high temperature for the reaction, but also results in a large amount of by-products at the same time.

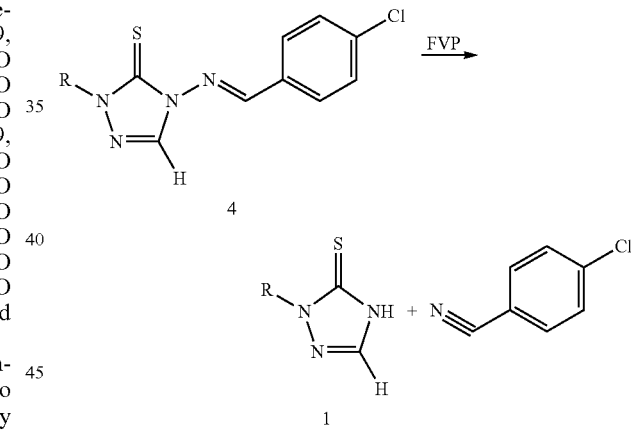

U.S. Pat. No. 6,559,317 disclosed a deprotonation method for the preparation of 1,2,4-triazole-3-thione compound 1 using $FeCl_3$ to oxidize triazole 5. The starting material 5 of this method is unstable and difficult to prepare. In addition, treatment of the iron-containing waste is an environmental problem.

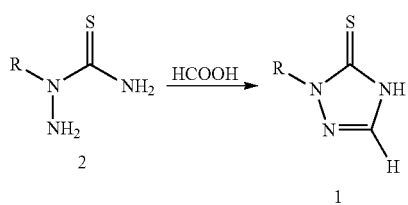

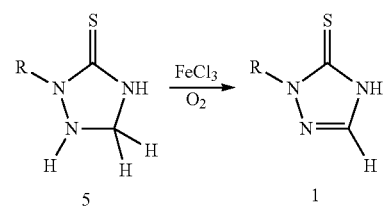

SUMMARY

The present application discloses a method of synthesizing 1,2,4-triazole-3-thione compounds and intermediates thereof in order to solve the problems in the prior art.

Method of synthesizing 1,2,4-triazole-3-thione compounds comprises the following steps:

step 1: reacting compound 6 or 6' with compound 7 or 7' to produce compound 8 or 8', as shown in the following reaction scheme:

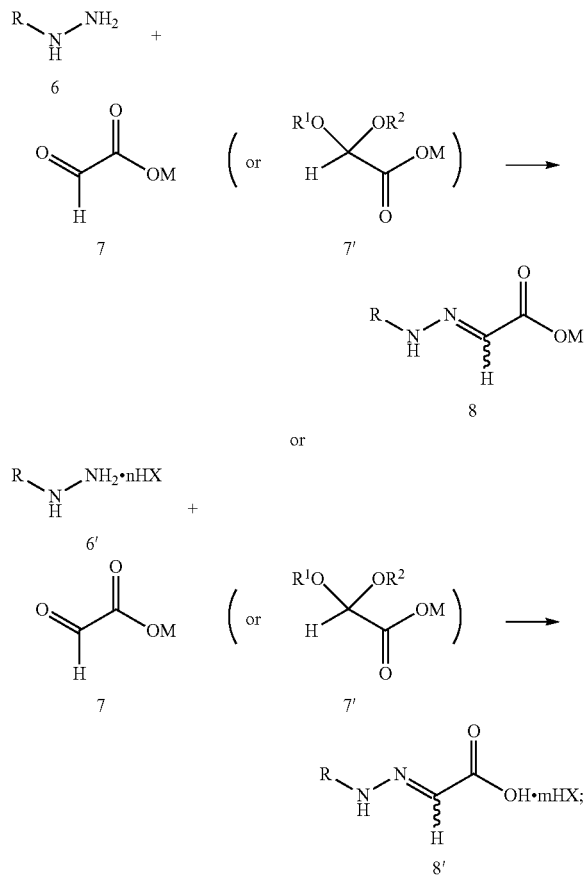

wherein:

R is selected from a $C_1$-$C_{18}$ alkyl group, a $C_6$-$C_{18}$ aryl group or a $C_5$-$C_6$ heteroaryl group containing oxygen, nitrogen or sulfur; and $R^1$,$R^2$ is independently selected from hydrogen or a $C_1$-$C_6$ alkyl group, or $R^1$,$R^2$ taking together to form a ring is selected from dimethylene, trimethylene, tetramethylene or pentamethylene group;

n is 0.5, 1 or 2;

HX is selected from a hydrohalic acid, sulfuric acid or phosphoric acid;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group; and m is 0 or 1;

step 2: reacting compound 8 or 8' with thiocyanate (M'SCN) to produce 1,2,4-triazole-3-thione compound 1, as shown in the following reaction scheme:

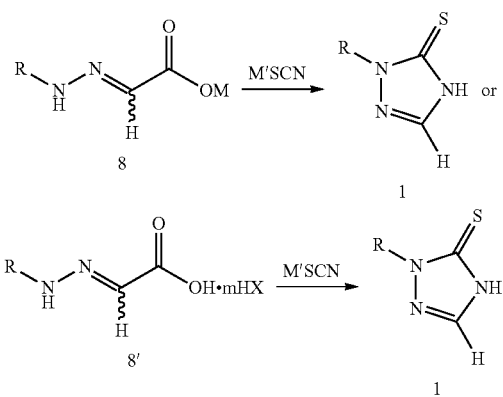

wherein:

R is selected from a $C_1$-$C_{18}$ alkyl group, a $C_6$-$C_{18}$ aryl group or a $C_5$-$C_6$ heteroaryl group containing oxygen, nitrogen or sulfur;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

HX is selected from a hydrohalic acid, sulfuric acid or phosphoric acid.

Specifically, step 1 is carried out in the presence or absence of a solvent, and the solvent is selected from water, acetonitrile, tert-butanol, dichloromethane, DMF, DMSO and toluene or their mixture. A molar ratio of compound 6 or 6' to compound 7 or 7' is preferably 1:1-10. A reaction temperature in step 1 is preferably 0-40° C.

Step 2 is preferably carried out in the presence of an acid, and the acid can be used as a catalyst or directly as a solvent. The acid is preferably an organic acid selected from formic acid, acetic acid, trifluoroacetic acid, methanesulfonic acid and p-toluenesulfonic acid or their mixture. A molar ratio of the acid to compound 8 or 8' is preferably 0.01-100:1. The molar ratio of compound 8 or 8' to the thiocyanate in step 2 is preferably 1:1-5. A reaction temperature in step 2 is preferably 50-80° C.

Steps 1 and 2 can be carried out in a stepwise or a one-pot manner.

A method of synthesizing 1,2,4-triazole-3-thione compound 1 comprises the following step:

reacting compound 8 or 8' with thiocyanate (M'SCN) to produce 1,2,4-triazole-3-thione compound 1, as shown in the following reaction scheme:

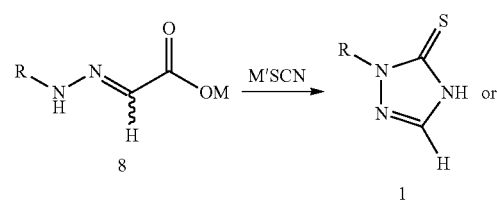

-continued

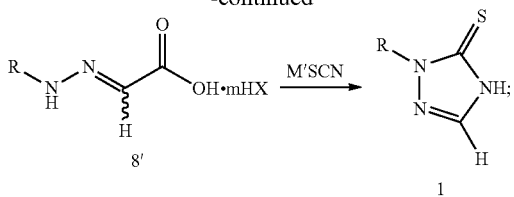

wherein:

R is selected from a $C_1$-$C_{18}$ alkyl group, a $C_6$-$C_{18}$ aryl group or a $C_5$-$C_6$ heteroarylgroup containing oxygen, nitrogen or sulfur;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is selected from an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

HX is selected from a hydrohalic acid, sulfuric acid or phosphoric acid.

Specifically, this reaction is preferably carried out in the presence of an acid, and the acid can be used as a catalyst or directly as a solvent. The acid is preferably an organic acid selected from formic acid, acetic acid, trifluoroacetic acid, methanesulfonic acid and p-toluenesulfonic acid or their mixture. A molar ratio of the acid to compound 8 or 8' is preferably 0.01-100:1. The molar ratio of compound 8 or 8' to the thiocyanate is preferably 1:1-5, and a reaction temperature is preferably 50-80° C.

The present application provides a compound 8 of formula (I):

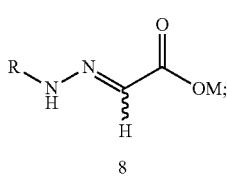

wherein:

R is selected from a $C_1$-$C_{18}$ alkyl group, a $C_6$-$C_{18}$ aryl group, or a $C_5$-$C_6$ heteroaryl group containing oxygen, nitrogen or sulfur, excluding a methyl group, a phenyl and a benzyl group; and M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group.

The present application further provides a compound 8' of formula (II):

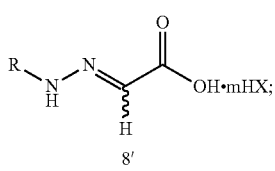

wherein:

R is selected from a $C_1$-$C_{18}$ alkyl group, a $C_6$-$C_{18}$ aryl group, or a $C_5$-$C_6$ heteroaryl group containing oxygen, nitrogen or sulfur, excluding a methyl group, a phenyl and a benzyl group;

m is 0 or 1; and

HX is selected from a hydrohalic acid, sulfuric acid or phosphoric acid.

A method of synthesizing 1,2,4-triazole-3-thione compounds and intermediates thereof has the following advantages:

1. The raw materials involved in the present invention are readily available, and the reaction is very specific in terms of regioselectivity, resulting in minimum by-product formation and high product yield.

2. There are neither specific requirements for special equipment nor special operations such as high vacuum, high temperature, anhydrous and oxygen-free manipulations.

3. The process is simple and generates minimum wastes, suitable for industrial production.

DETAILED DESCRIPTION OF EMBODIMENTS

The following embodiments are intended to illustrate the features of the present invention. The scope of the application is not limited to these embodiments.

Example 1: Synthesis of 2-(2-phenylhydrazono) acetic acid

To a 500 mL reaction flask were added 28.9 g of phenylhydrazine hydrochloride, 300 mL of water and 75 mL of acetonitrile. Then 29.6 g of 50% glyoxylic acid solution was added dropwise. The reaction mixture was stirred at room temperature. After the reaction was complete, the reaction mixture was filtered, washed with water and dried to give 29.0 g of product as a solid (88% yield).

$^1$H NMR (δ, DMSO-d6):11.125; (m, 1H), 7.283-7.252; (m, 2H), 7.157; (s, 1H), 7.123-7.107; (d, 2H), 6.896-6.866; (t, 1H); MS: m/z=165.1; ([M+1]$^+$).

Example 2: Synthesis of 2-(2-phenylhydrazono) acetic acid

To a 500 mL reaction flask were added 43.4 g of phenylhydrazine hydrochloride and 350 mL of water. Then 57.6 g of 50% sodium glyoxylate solution was added dropwise. The reaction mixture was stirred at room temperature. After the reaction was complete, the reaction mixture was filtered, washed with water and dried to give 45.3 g of product as a solid (92% yield).

Example 3: Synthesis of 2-(3-chloropyridine hydrazono) acetic acid

To a 100 mL reaction flask were added 5.0 g of 3-chloro-2-hydrazylpyridine and 50 mL of water. Then 26 g of 50% glyoxylic acid solution was added dropwise. The reaction mixture was stirred at room temperature. After the reaction was complete, the reaction mixture was filtered, washed with water and dried to give 6.6 g of product as a solid (95% yield).

$^1$H NMR (δ, DMSO-d6): 12.648; (s, 1H), 11.092; (s, 1H), 8.230-8.215; (m, 1H), 7.855-7.832; (m, 1H), 7.706; (s, 1H), 7.003-6.972; (m, 1H); MS: m/z=200.02; ([M+1]$^+$).

Example 4: Synthesis of Sodium 2-(2-phenylhydrazono) acetate

To a 100 mL reaction flask were added 5.0 g of phenylhydrazine and 50 mL of water. Then 8.9 g of 50% sodium glyoxylate solution was added dropwise. The reaction mixture was stirred at room temperature. After the reaction was complete, the solvent was removed. 7.6 g of a solid product was obtained by desiccation (100% yield).

Example 5: Synthesis of 2-(2-methylhydrazono) acetic acid

To a 100 mL reaction flask were added 5.0 g of methylhydrazine sulfate and 50 mL of water. Then 5.7 g of 50% glyoxylic acid solution was added dropwise. The reaction mixture was stirred at room temperature. After the reaction was complete, the reaction mixture was filtered, washed with water and dried to give 3.4 g of product as a solid (95% yield).
$^1$H NMR (δ, DMSO-d6): 11.975; (s, 1H), 6.463-6.461; (d, 1H), 4.995; (s, 1H), 2.835; (s, 3H); MS: m/z=103.0; ([M+1]$^+$).

Example 6: Synthesis of 2-(2-benzylhydrazono) acetic acid

To a 250 mL reaction flask were added 11.7 g of benzylhydrazine dihydrochloride, 100 mL of water and 15 mL of acetonitrile. Then 9.5 g of 50% glyoxylic acid solution was added dropwise. The reaction mixture was stirred at room temperature. After the reaction was complete, the reaction mixture was filtered, washed with water and dried to give 9.4 g of product as a solid (88% yield).
$^1$H NMR (δ, DMSO-d6): 11.994; (s, 1H), 7.370-7.333; (t, 2H), 7.290-7.253; (t, 1H), 7.2256-7.208; (d, 2H), 6.397; (s, 1H), 5.339; (s, 1H), 4.700; (s, 2H); MS: m/z=179.1; ([M+1]$^+$).

Example 7: Synthesis of 2-(2-benzylhydrazono) acetic acid

To a 50 mL reaction flask were added 2.34 g of benzylhydrazine dihydrochloride and 20 mL of water. Then 1.18 g of glyoxylic acid monohydrate was added in portions. The reaction mixture was stirred at room temperature. After the reaction was complete, the reaction mixture was filtered, washed with water and dried to give 1.94 g of product as a solid (91% yield).

Example 8: Synthesis of 2-{2-[2-(1-chlorocyclopropyl)-3-(2-chlorophenyl)-2-hydroxypropyl] hydrazono} acetic acid To a 250 mL reaction flask were added 13.7 g of 2-(1-chlorocyclopropyl)-1-(2-chlorophenyl)-3-hydrazinopropan-2-ol and 100 mL of water. Then 4.7 g of glyoxylic acid monohydrate was added in portions. The reaction mixture was stirred at room temperature. After the reaction was complete, the reaction mixture was filtered, washed with water and dried to give 14.5 g of product as a solid (88% yield).

Example 9: Synthesis of Sodium 2-(2-phenylhydrazono) Acetate

To a 500 mL reaction flask were added 50 g of 2-(2-phenylhydrazono) acetic acid and 300 mL of ethanol. Then 24.4 g of a 50% sodium hydroxide solution was added dropwise. The reaction mixture was stirred at room temperature. After the reaction was complete, the reaction mixture was concentrated, slurried with ethanol, filtered and dried to give 56.1 g of product as a solid (99% yield).

Example 10: Synthesis of 2-{2-[2-(1-chlorocyclopropyl)-3-(2-chlorophenyl)-2-hydroxypropyl] hydrazono} acetic acid hemisulfate To a 25 mL reaction flask were added 1.37 g of 2-(1-chlorocyclopropyl)-1-(2-chlorophenyl)-3-hydrazinopropan-2-ol and 15 mL of acetonitrile. Then 0.96 g of 50% glyoxylic acid solution and 0.25 g of concentrated sulfuric acid were added dropwise. The reaction mixture was stirred at room temperature. After the reaction was complete, the solvent was removed. 1.89 g of a solid product was obtained by lyophilization (99% yield).

Example 11: Synthesis of 2-{2-[2-(1-chlorocyclopropyl)-3-(2-chlorophenyl)-2-hydroxypropyl] hydrazono} acetic acid hemisulfate To a 250 mL reaction flask were added 3.3 g of 2-{2-[2-(1-chlorocyclopropyl)-3-(2-chlorophenyl)-2-hydroxypropyl] hydrazono} acetic acid and 10 mL of acetonitrile. Then 0.5 g of concentrated sulfuric acid was added dropwise. The reaction mixture was stirred at room temperature. After the reaction was complete, the solvent was removed. 3.8 g of a solid product was obtained by lyophilization (99% yield).

Example 12: Synthesis of 2-{2-[2-(1-chlorocyclopropyl)-3-(2-chlorophenyl)-2-hydroxypropyl] hydrazono} acetic acid To a 250 mL reaction flask was added 15.5 g of 2-(1-chlorocyclopropyl)-1-(2-chlorophenyl)-3-hydrazinopropan-2-ol hydrochloride. Then 75 g of 50% glyoxylic acid solution was added dropwise. The reaction mixture was stirred at room temperature. After the reaction was complete, the reaction mixture was filtered, washed and dried to give 16.4 g of product as a solid (99% yield).
$^1$H NMR (δ, CDCl$_3$): 7.456-7.437; (m, 1H), 7.405-7.386; (m,1H), 7.271-7.252; (m, 1H), 7.245-7.223; (m, 1H), 6.971-6.899; (t, 1H), 6.781; (s, 1H), 3.906-3.898, 3.878-3.869; (dd, 1H), 3.547-3.519; (d, 1H), 3.519-3.508, 3.491-3.480; (dd, 1H), 3.211-3.183; (d, 1H), 2.506; (s, 2H), 1.175-1.134; (m, 1H), 0.964-0.852; (m, 3H); MS: m/z=330.9; ([M+1]$^+$).

Example 13: Synthesis of 2-phenyl-1,2,4-triazole-3-thione

To a 250 mL reaction flask were added 4.9 g of 2-(2-phenylhydrazono) acetic acid, 8.7 g of potassium thiocyanate and 50 mL of trifluoroacetic acid. The reaction was heated to 50° C. After the reaction was complete, the reaction mixture was concentrated. 4.4 g of a solid product was obtained by adding with toluene, washing with water and distillation (83% yield).
$^1$H NMR (δ, DMSO-d6): 14.193; (s, 1H), 10.005; (s, 1H), 7.826-7.810; (d, 2H), 7.600-7.569; (m, 2H), 7.492-7.463; (m, 1H); MS: m/z=178.0; ([M+1]$^+$).

Example 14: Synthesis of 2-benzyl-1,2,4-triazole-3-thione

To a 250 mL reaction flask were added 9 g of 2-(2-benzylhydrazono) acetic acid, 4 g of sodium thiocyanate and 100 mL of acetic acid. The reaction was heated to 80° C. After the reaction was complete, the reaction mixture was concentrated. 8.7 g of a solid product was obtained by adding with toluene, washing with water and distillation (91% yield).

¹H NMR (δ, DMSO-d6): 13.565; (s, 1H), 8.355; (s, 1H), 7.368-7.144; (m, 5H), 5.297; (s, 2H).

Example 15: synthesis of 2-(3-chloropyridin-2-yl)-1,2,4-triazole-3-thione

To a 250 mL reaction flask were added 6.0 g of 2-(3-chloropyridinehydrazono) acetic acid hydrochloride, 11.4 g of ammonium thiocyanate and 50 mL of trifluoroacetic acid. The reaction was heated to 80° C. After the reaction was complete, the reaction mixture was concentrated. 5.0 g of a solid product was obtained by adding with toluene, washing with water and distillation (93% yield).

¹H NMR (δ, DMSO-d6): 7.904-7.889; (m, 1H), 7.568-7.545; (m, 1H), 6.564-6.533; (m, 1H), 6.234; (s, 2H); MS: m/z=213.0; ([M+1]⁺).

Example 16: Synthesis of 2-methyl-1,2,4-triazole-3-thione

To a 250 mL reaction flask were added 9.2 g of 2-(2-methylhydrazono) acetic acid, 14.6 g of sodium thiocyanate and 80 mL of acetic acid. The reaction was heated to 80° C. After the reaction was complete, the reaction mixture was concentrated. 9.3 g of a solid product was obtained by adding with toluene, washing with water and distillation (90% yield).

¹H NMR (δ, DMSO-d6): 8.733; (s, 1H), 6.039; (s, 1H), 3.631; (s, 3H).

Example 17: synthesis of 2-phenyl-1,2,4-triazole-3-thione

To a 250 mL reaction flask were added 16.8 g of sodium 2-(2-phenylhydrazono) acetate, 14.6 g of sodium thiocyanate, 80 mL of acetic acid and 8.7 g of methanesulfonic acid. The reaction was heated to 80° C. After the reaction was complete, the reaction mixture was concentrated. 14.9 g of a solid product was obtained by adding with toluene, washing with water and distillation (93% yield).

Example 18: Synthesis of 2-[2-(1-chlorocyclopropyl)-3-(2-chlorophenyl)-2-hydroxypropyl]-1,2,4-triazole-3-thione To a 250 mL reaction flask were added 16.5 g of 2-{2-[2-(1-chlorocyclopropyl)-3-(2-chlorophenyl)-2-hydroxypropyl] hydrazono} acetic acid, 6.1 g of sodium thiocyanate and 80 mL of acetic acid. The reaction was heated to 80° C. After the reaction was complete, the reaction mixture was concentrated. 16.3 g of a solid product was obtained by adding with toluene, washing with water and distillation (95% yield).

¹H NMR (δ, CDCl₃): 12.300; (s, 1H), 7.856; (s,1H), 7.549-7.544, 7.534-7.530; (dd, 1H), 7.377-7.374, 7.362-7.358; (dd, 1H), 7.242-7.183; (m, 2H), 4.802-4.773; (d, 1H), 4.510-4.481; (d, 1H), 4.212; (s, 1H), 3.621-3.594; (d, 1H), 3.193-3.166; (d, 1H), 0.943-0.922; (m, 1H), 0.885-0.767; (m, 3H); MS: m/z=343.9; ([M+1]⁺).

Example 19: Synthesis of 2-[2-(1-chlorocyclopropyl)-3-(2-chlorophenyl)-2-hydroxypropyl]-1,2,4-triazole-3-thione To a 25 mL reaction flask were added 1.89 g of 2-{2-[2-(1-chlorocyclopropyl)-3-(2-chlorophenyl)-2-hydroxypropyl] hydrazono} acetic acid hemisulfate, 0.62 g of sodium thiocyanate and 10 mL of acetic acid. The reaction was heated to 50° C. After the reaction was complete, the reaction mixture was concentrated. 1.43 g of a solid product was obtained by adding with toluene, washing with water and distillation (83% yield).

Example 20: Synthesis of 2-[2-(1-chlorocyclopropyl)-3-(2-chlorophenyl)-2-hydroxypropyl]-1,2,4-triazole-3-thione To a 100 mL reaction flask were added 0.93 g of 2-(1-chlorocyclopropyl)-1-(2-chlorophenyl)-3-hydrazinopropan-2-ol hydrochloride, 15 mL of acetonitrile, 0.55 g of a 50% glyoxylic acid solution and 0.24 g of sodium thiocyanate. The reaction was heated to 60° C. After the reaction was complete, 10 mL of water was added, the pH of the reaction mixture was adjusted to 2. The phases were separated, the aqueous phase was extracted using toluene, the organic phases were combined and concentrated to give 0.92 g of product as a solid (89% yield).

What is claimed is:
1. A method of synthesizing 1,2,4-triazole-3-thione compounds 1, comprising:
step 1: reacting compound 6 or 6' with compound 7 or 7' to produce compound 8 or 8', as shown in the following reaction scheme:

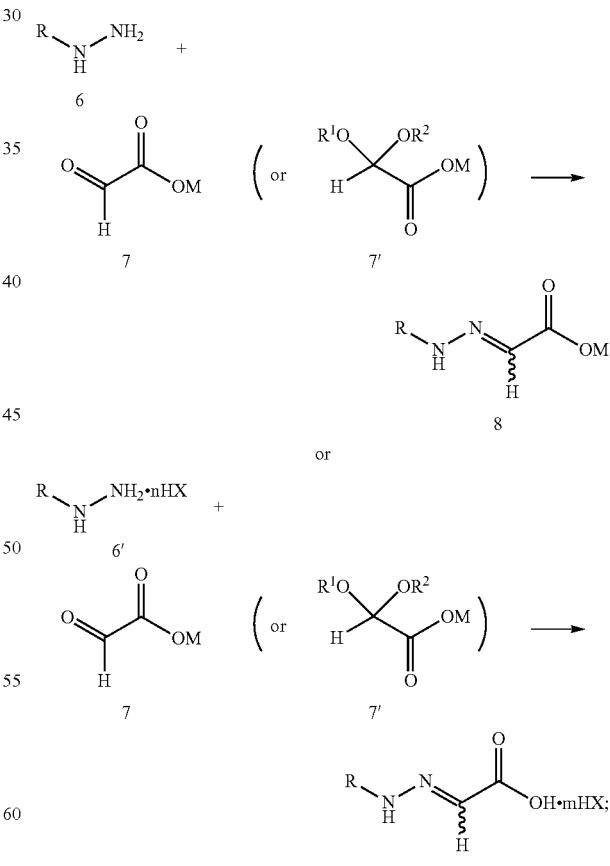

wherein:
R is selected from a $C_1$-$C_{18}$ alkyl group, a $C_6$-$C_{18}$ aryl group or a $C_5$-$C_6$ heteroaryl group containing oxygen, nitrogen or sulfur; and $R^1, R^2$ is independently selected from hydrogen or a $C_1$-$C_6$ alkyl group, or $R^1, R^2$ taking together to from a ring is selected from dimethylene, trimethylene, tetramethylene or pentamethylene;

n is 0.5, 1 or 2;

HX is selected from a hydrohalic acid, sulfuric acid or phosphoric acid;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group; and m is 0 or 1;

step 2: reacting compound 8 or 8' with thiocyanate (M'SCN) to produce 1,2,4-triazole-3-thione compound 1, as shown in the following reaction scheme:

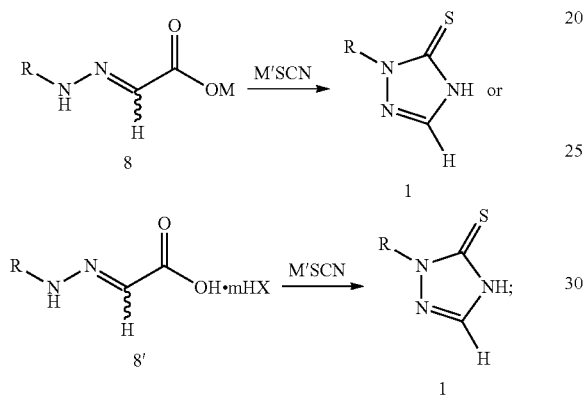

wherein:

R is selected from a $C_1$-$C_{18}$ alkyl group, a $C_6$-$C_{18}$ aryl group or a $C_5$-$C_6$ heteroaryl group containing oxygen, nitrogen or sulfur;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

HX is selected from a hydrohalic acid, sulfuric acid or phosphoric acid.

2. The method of claim 1, wherein step 1 is carried out in the presence or absence of a solvent; a molar ratio of compound 6 or 6' to compound 7 or 7' is 1:1-10; and a reaction temperature in step 1 is 0-40° C.

3. The method of claim 2, wherein the solvent is selected from water, acetonitrile, tert-butanol, dichloromethane, DMF, DMSO and toluene or mixture thereof.

4. The method of claim 1, wherein steps 1 and 2 are carried out in a stepwise or a one-pot manner.

5. A method of synthesizing 1,2,4-triazole-3-thione compound 1, comprising:

reacting compound 8 or 8' with thiocyanate (M'SCN) to produce 1,2,4-triazole-3-thione compound 1, as shown in the following reaction scheme:

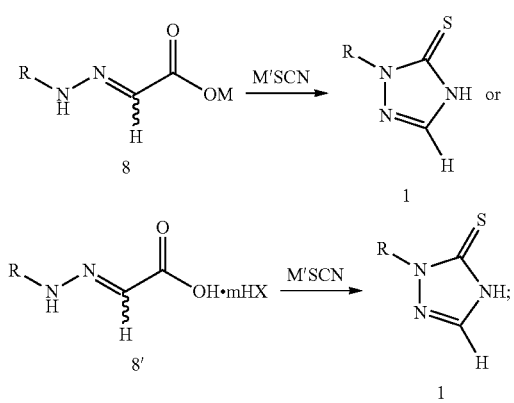

wherein:

R is selected from a $C_1$-$C_{18}$ alkyl group, a $C_6$-$C_{18}$ aryl group or a $C_5$-$C_6$ heteroaryl group containing oxygen, nitrogen or sulfur;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is selected from an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

HX is selected from a hydrohalic acid, sulfuric acid or phosphoric acid.

6. The method of claim 1, wherein in step2, compound 8 or 8' is reacted with M'SCN in the presence of an acid; a molar ratio of compound 8 or 8' to M'SCN is 1:1-5; and a reaction temperature is 50-80° C.

7. The method of claim 5, wherein compound 8 or 8' is reacted with M'SCN in the presence of an acid; a molar ratio of compound 8 or 8' to M'SCN is 1:1-5; and a reaction temperature is 50-80° C.

8. The method of claim 6, wherein the acid is an organic acid; and a molar ratio of the acid to compound 8 or 8' is 0.01-100:1.

9. The method of claim 7, wherein the acid is an organic acid; and a molar ratio of the acid to compound 8 or 8' is 0.01-100:1.

10. The method of claim 8, wherein the organic acid is selected from formic acid, acetic acid, trifluoroacetic acid, methanesulfonic acid and p-toluenesulfonic acid or their mixture.

11. The method of claim 9, wherein the organic acid is selected from formic acid, acetic acid, trifluoroacetic acid, methanesulfonic acid and p-toluenesulfonic acid or mixture therrof.

12. A compound 8 of formula (I):

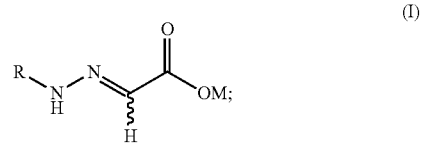

wherein:

R is selected from a $C_1$-$C_{18}$ is alkyl group, a $C_6$-$C_{18}$ is aryl group, or a $C_5$-$C_6$ heteroaryl group containing oxygen, nitrogen or sulfur, excluding a methyl group, a phenyl, a benzyl group, and a $C_5$-$C_6$ heteroaryl group containing nitrogen; and M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group.

13. A compound 8' of formula (II):

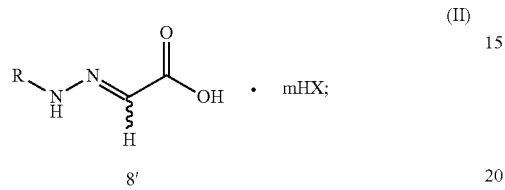

(II)

8'    · mHX;

wherein:

R is selected from a $C_1$-$C_{18}$ alkyl group, a $C_6$-$C_{18}$ aryl group, or a $C_5$-$C_6$ heteroaryl group containing oxygen, nitrogen or sulfur, excluding a methyl group, a phenyl, a benzyl group and a pyridyl group, and a $C_5$-$C_6$ heteroaryl group containing nitrogen;

m is 1; and

HX is selected from a hydrohalic acid, sulfuric acid or phosphoric acid.

* * * * *